(12) United States Patent
Alper

(10) Patent No.: US 9,504,941 B2
(45) Date of Patent: *Nov. 29, 2016

(54) VISUAL QUALITY INDICATOR FOR AQUEOUS STREAMS

(71) Applicant: Mycelx Technologies Corporation, Gainesville, GA (US)

(72) Inventor: Hal Alper, Flowery Branch, GA (US)

(73) Assignee: MYCELX TECHNOLOGIES CORPORATION, Duluth, GA (US)

( * ) Notice: Subject to any disclaimer, the term of this patent is extended or adjusted under 35 U.S.C. 154(b) by 747 days.

This patent is subject to a terminal disclaimer.

(21) Appl. No.: 13/766,314

(22) Filed: Feb. 13, 2013

(65) Prior Publication Data

US 2013/0175000 A1 Jul. 11, 2013

Related U.S. Application Data

(63) Continuation-in-part of application No. 13/475,238, filed on May 18, 2012, now Pat. No. 8,394,265, which is a continuation of application No. 12/079,244, filed on Mar. 25, 2008, now Pat. No. 8,187,459.

(60) Provisional application No. 60/920,193, filed on Mar. 27, 2007.

(51) Int. Cl.
| | |
|---|---|
| *B01D 35/143* | (2006.01) |
| *G01N 33/18* | (2006.01) |
| *F28F 27/00* | (2006.01) |
| *B63J 4/00* | (2006.01) |
| *C02F 1/28* | (2006.01) |
| *G01N 21/64* | (2006.01) |
| *C02F 103/00* | (2006.01) |
| *C02F 101/32* | (2006.01) |

(52) U.S. Cl.
CPC ............ *B01D 35/143* (2013.01); *B63J 4/002* (2013.01); *B63J 4/004* (2013.01); *B63J 4/006* (2013.01); *C02F 1/288* (2013.01); *F28F 27/00* (2013.01); *G01N 33/1833* (2013.01); *B01J 2220/49* (2013.01); *C02F 2101/32* (2013.01); *C02F 2103/008* (2013.01); *G01N 21/64* (2013.01)

(58) Field of Classification Search
None
See application file for complete search history.

(56) References Cited

U.S. PATENT DOCUMENTS 4,032,453 A * 6/1977 Pedone ..................... 210/266
4,512,890 A 4/1985 Medbury
(Continued)

OTHER PUBLICATIONS

U.S. Appl. No. 13/475,238, filed May 18, 2012, Alper.
(Continued)

*Primary Examiner* — Terry Cecil
(74) *Attorney, Agent, or Firm* — Sutherland Asbill & Brennan LLP

(57) ABSTRACT

A visual indicator device and method for determining the presence of oily contaminants in an aqueous stream are provided. The device includes a filtration status chamber for receiving and discharging the aqueous stream, and a transparent wall enabling viewing of the chamber interior. A fluid-pervious filtration media within the chamber is infused with an absorption composition at which the contaminant on contact with the media is immobilized. The media has a surface viewable through a transparent wall of the filtration status chamber, and the stream flow path causes the stream to impinge at the media via the surface, whereby the contaminants collect selectively at the media surface and are highly visible through the transparent wall.

7 Claims, 5 Drawing Sheets

(56) References Cited

U.S. PATENT DOCUMENTS

| | | |
|---|---|---|
| 4,740,296 A * | 4/1988 | Roman .......................... 210/94 |
| 5,139,679 A | 8/1992 | Pan et al. |
| 5,401,404 A | 3/1995 | Strauss |
| 5,437,793 A | 8/1995 | Alper |
| 5,698,139 A | 12/1997 | Alper |
| 5,837,146 A | 11/1998 | Alper |
| 5,961,823 A | 10/1999 | Alper |
| 6,180,010 B1 | 1/2001 | Alper |
| 6,391,626 B1 | 5/2002 | Adams et al. |
| 6,475,393 B2 | 11/2002 | Alper |
| 7,264,721 B2 | 9/2007 | Alper |
| 7,264,722 B2 | 9/2007 | Alper |
| 7,597,809 B1 | 10/2009 | Roberts |
| 7,688,428 B2 | 3/2010 | Pearlman |
| 8,187,459 B2 | 5/2012 | Alper |
| 8,394,265 B2 * | 3/2013 | Alper .............................. 210/93 |
| 2006/0027507 A1 | 2/2006 | van Leeuwen et al. |

OTHER PUBLICATIONS

Hal Alper, Title: "Removal of Oils and Organic Compounds from water and Air with Mycelx HRM (Hydrocarbon Removal Matrix) Technology"; Federal Facilities Environmental Journal Fall 2003, pgs.

Hal Alper, Title: Use of Polymeric Surfactant Infused Substrates in Removal of Emulsions and Aromatic Hydrocarbons from Aqueous Waste Streams, Naval Engineers Journal, vol. 112, No. 4, pp. 177-191, Jul. 2000.

* cited by examiner

VISUAL QUALITY INDICATOR FOR AQUEOUS STREAMS

CROSS-REFERENCE TO RELATED APPLICATIONS

This application is a continuation-in-part application of U.S. patent application Ser. No. 13/475,238, filed May 18, 2012,now U.S. Pat. No. 8,394,265, which is a continuation application of U.S. patent application Ser. No. 12/079,244, filed Mar. 25, 2008, now U.S. Pat. No. 8,187,459, which claims priority from U.S. Provisional Patent Application Ser. No. 60/920,193, filed Mar. 27, 2007, each of which is incorporated herein by reference in its entirety.

FIELD OF THE INVENTION

This disclosure relates generally to an apparatus and methodology for visually determining the presence of oily contaminants suspended or dispersed in an aqueous stream, and more specifically relates to a visual indicator device for visually examining an aqueous stream to determine the presence therein of such contaminants.

BACKGROUND OF THE INVENTION

The present invention is applicable to any type of aqueous stream or effluent and provides generally an apparatus and methodology for visually determining the presence of oily contaminants suspended or dispersed in an aqueous stream. The issues associated with marine bilgewater discharge which are presented in detail herein provide an excellent specific illustration of an environment to which the broader present invention is applicable. Over the past two decades, U.S. regulations dealing with bilgewater discharge for all types of vessels have grown increasingly stringent. Environmental technology has struggled to keep pace but until recently, no removal method has been capable of eliminating sheen and extracting substantially all harmful contaminants from bilgewater. Federal regulations set a high standard for bilgewater discharge, because even tiny amounts of bilgewater oil have been demonstrated to kill huge numbers of lobster eggs, which is just one example of the enormous threat to aquatic life.

The Federal Water Pollution Act, also known as the Clean Water Act, accordingly proscribes even the appearance of a visible sheen on the water, punishable by a $5,000 penalty. More specifically, the act "prohibits the discharge of oil or oily waste into or upon the navigable waters of the United States or the waters of the contiguous zone if such discharge causes a film or sheen upon, or causes a sludge or emulsion beneath the surface of the water." From an environmental perspective, the increased regulatory activity in bilgewater discharge limits is warranted. The cumulative effect of vessels ranging from small recreational boats to large surface ships dumping even small amounts of bilgewater could wreak damage upon fragile aquatic ecosystems and likely has already done so.

In the instance of marine bilgewater discharge, the primary sources of the contaminants are vessel propulsion systems and auxiliary systems that use fuels, lubricants, hydraulic fluid, antifreeze, solvents and cleaning chemicals. Certain waste streams such as steam condensate, boiler blowdown, drinking fountain water, and sink drainage located in various machinery spaces can also drain to the bilge.

Currently, commercial and military surface ships primarily employ two different methods in dealing with bilgewater treatment and removal. Many of these vessels use oil-water separator systems to reduce the oil content of bilgewater prior to overboard discharge. Most of these large vessels also have onboard systems for collecting and transferring bilgewater to a holding tank for later removal and disposal on shore.

In the present inventor's U.S. Pat. No. 6,475,393 (see also related U.S. Pat. No. 6,180,010), it is disclosed that the compositions described in the inventor's U.S. Pat. Nos. 5,437,793; 5,698,139; and 5,837,146, and 5,961,823 (all of which disclosures are hereby incorporated by reference) have extremely strong affinities for the contaminants in oily bilgewater; and that when oily bilgewater streams containing these noxious contaminants are passed through filtration media incorporating these compositions, the contaminants are immobilized at the media. As a result, concentration levels of the contaminants in the filtrate may be reduced to very low values, in some instances below detectable limits in a single pass. This feature not only enables ready removal of oils, greases, and similar materials from the bilgewater, but also allows removal of pernicious, slightly soluble organic compounds such as benzene, toluene, xylene, halogenated hydrocarbons, ethoxylated glycols, and the like. These noxious contaminants are among the more difficult compounds to remove from water, and indeed most are carcinogenic. The solubility of the foregoing substances renders most prior art physical separation methods generally ineffective and causes formation of stable and pseudostable oily emulsions (micelle size of 400 micrometers or less), which also do not respond well to gravity separation due to neutral buoyancy.

In accordance with these prior patents, the bilgewater can be passed through one or more filters incorporating the principles of the earlier inventions, prior to the bilgewater being actually discharged from the vessel. The filter or filters may simply be placed directly in the bilgewater discharge line, for example, downstream of the bilgewater pump effecting the discharge flow. In a test of a typical such installation, the test results included removal of all sheen and visible discharge.

More specifically, the method of the prior invention may be described as one of passing the bilgewater through a fluid-pervious filtration media which has been infused with an absorption composition comprising a homogeneous thermal reaction product of an oil component selected from the group consisting of glycerides, fatty acids, alkenes, and alkynes, and a methacrylate or acrylate polymer component; the contaminant being thereby immobilized at the media. For convenience these absorption compositions may hereinafter be referred to as "MACs", a term derived from "Mycelx absorbent compositions", where "Mycelx" is not used as a technical descriptor but merely as a reference to the assignee of the aforementioned patents pertaining to the said compositions and methodology. It will be appreciated that the MACs used in the present invention are not limited to the specific absorption compositions disclosed in the aforementioned U.S. patents, but also may include for example, additional compositions falling within the aforementioned description of the compositions, such as improvements upon the previously patented compositions which yet remain within the technical description stated immediately above in this paragraph.

Filter configurations incorporating the MACs may be based on various water permeable substrates, such as shredded, spun or otherwise configured polypropylene or shredded or spun cellulose, which substrates are infused or otherwise treated with the absorbent compositions, which are then cured. These substrates may then be packed or otherwise disposed in a cartridge or canister filter, or the substrates can be formed into cured and infused bag filters which can be emplaced in canisters through which the contaminated bilgewater is flowed. Similarly, the said absorbent compositions can be incorporated into or upon other filtering substrates and media if desired, including for example, paper, compressed pulp materials, particulate porous foamed plastics, mineral particulates such as perlite and vermiculite, and particulate, fibrous or porous ceramic or porous (for example, sintered) metal substrates and media.

In the course of utilizing bilgewater filtration systems, including those based upon the foregoing principles, it is often difficult to determine the quality of effluent from oily water separators without relying on some detector response, sensor reading, or the like. Moreover, it is often not possible even to determine visually if such detectors are operating properly. The capability to perform a rapid visual inspection of a filtration system would be useful for quickly determining when the capacity of the filtration system has been exceeded. However, the inability to perform simple visual inspections has led to accidental oily bilge water discharge and can even lead to criminal prosecution of the individuals responsible. In the case of oily water treatment devices, it is not possible to effectively use transparent sight gauges or glass indicators on the housings or in the connecting piping, due to the tendency of the surfaces over which the discharge flows to become opaque from oily fouling. Difficulties such as this arise not only in bilgewater, but also in numerous aqueous process streams where it is at least equally important to be rapidly made aware of the presence of oily contaminants. The presence of oily contaminants can arise for many reasons other than filtration failure or overload, as for example from accidental or other unintended leakage of oily contaminants into the process stream.

Therefore, what is needed generally is an apparatus and/or method for visually determining the presence of oily contaminants, including those very small size oily droplet which may be present as or behave as particulates suspended or dispersed in an aqueous stream. More specifically, what is needed is a indicator device and method that allows for visually examining any aqueous stream to determine the presence therein of such contaminants. The capability to perform a rapid visual inspection of a filtration system would be useful for quickly determining when the capacity of any aqueous filtration system has been exceeded or when there has been any type of failure of the system. This may be particularly important in an industrial process arrangement that employs a bank of individual operating units connected in series and/or in parallel that share some commonality, in which a small oily discharge or leak in any individual unit is difficult to locate, but can be highly problematic.

SUMMARY OF THE INVENTION

Now in accordance with the present disclosure, there is provided a visual quality indicator ("VQI" or simply "visual indicator") for determining the presence of oily contaminants in an aqueous stream. The visual indicator can be positioned at any point in the flow stream where a visual determination is sought regarding the presence and degree of the oily contaminants. For example, a bypass or shunt line is typically connected to divert a test stream from the primary stream of interest and return the diverted flow back to the primary stream. The visual quality indicator can include at least a first status chamber connected inline at the bypass line or elsewhere in the aqueous stream where the stream quality is to be evaluated. The status chamber includes a filtration media adapted to absorb and thereby immobilize the oily contaminants, and a transparent outer wall to enable viewing of the interior of the chamber. The filtration media is preferably a fluid-pervious filtration media as referenced in the applicant's above applications and patent, which has thus been infused with a MAC as also referenced; that is, an absorption composition comprising a homogeneous thermal reaction product of an oil component selected from the group consisting of glycerides, fatty acids, alkenes, and alkynes, and a methacrylate or acrylate polymer component. On contact with said media, the contaminant is thereby immobilized. The filtration media has a surface viewable through the transparent wall of the status chamber, and the stream flow path through the status chamber is such as to cause the stream to first impinge at the media via the viewable surface. Thus, the contaminants collect selectively at the media surface and are therefore highly visible through the transparent wall.

It will be appreciated that while the visual quality indicator described herein is utilized in evaluating the presence of oily contaminants in an aqueous stream, the origin of such stream can be highly variable. In the case of a primary stream being of interest, such as an output stream from an industrial process stream or filtration system, the actual test stream proceeding to the visual indicator can be that in a bypass branch from the primary stream. In other instances the indicator can be inserted directly in the flow of such a primary stream. Furthermore, it will be evident that one could take or divert a sample from a collection tank, a common water reservoir, or the like, and simply form that sample into a test stream for passage to and through the visual quality indicator as described herein.

The filtration status chamber, in one preferred embodiment, has means for channeling the flow received therein in a direction which proceeds from the chamber outside wall toward its central axis, whereby oily contaminants in the flow collect selectively at the outermost portions of the filtration media. In this manner, droplets of the oily contaminants in the flow collect and are immobilized selectively at the outer surface of the filter, where they are highly visible to an operator or inspector and can be easily visualized.

If desired, the filtration media may include a fluorescent or phosphorescent pigment or highly colored component, whereby the presence of captured oily contaminants is visually enhanced. Where the media responds to UV radiation, for example by including a fluorescent or phosphorescent pigment, the visual enhancement can be further augmented by rendering a UV light source incident on the media by passing such radiation through the substantially UV transparent walls of the status chamber.

Use of the preferred filtration media described herein is indeed especially significant in the present invention, in part because upon prolonged exposure to water without the presence of oil, conventional oil filtration media waterlogs, becoming hydrophilic and losing its ability to coalesce oily droplets. This state cannot be reversed and the waterlogged filtration media ceases to function. The MAC infused media of the present invention may also waterlog, but upon exposure to oil, the water is displaced and the media becomes totally hydrophobic and dry and retains its ability to attract and coalesce oil.

It should be emphasized that the MACs have been conclusively demonstrated in the inventor's prior patents and literature to be uniquely distinct compositions of matter. As will become apparent in the present specification, these MACs function in the invention in a way that is fundamentally different than the instrumentalities employed in any prior art, and therefore achieve in the invention fundamentally different and useful new results. Thus, oily droplets are captured at the outer surface of the filter, where the product of the MAC and captured oil is an immobilized viscoelastic mass, which allows for easy visual detection. Moreover, because of the nature of the immobilized viscoelastic mass that is formed upon oil capture by the MAC, the contaminants are permanently immobilized at the filtration media and do not re-release into the gaseous stream. Regarding the nature of the captured product, see inter alia the inventor's U.S. Pat. No. 5,961,823; and H. Alper, *Removal of oils and organic compounds from water and air with MYCELX HRM (Hydrocarbon Removal Matrix) technology*; Federal Facilities Environmental Journal 08/2003; 14(3):79-101, both of which are incorporated herein in their entireties.

The use of the MAC-infused filtration media in the instant disclosure accordingly provides unique aspects for its successful operation. This will be better appreciated by considering how oil might behave in water, as illustrated in Table 1 which reflects two states of 1 ppm concentration of oily contaminant, that is 1 g (gram) oil in 1 $m^3$ (cubic meter) of water. The first state is a single droplet of oil in 1 $m^3$ of water, wherein the droplet will behave as a liquid. The charge on a single droplet of this size (Table 1) is only about 0.2 coulomb/g; therefore, gravity dictated phenomena and the mass of the droplet are factors which drive the behavior of the large droplet and of the oily composition. In the case of this single large droplet, F(g), the gravitational forces acting on the droplet, are orders of magnitude greater than the electrostatic forces F(q) at this scale.

In the second state in which the droplets are separated into an oily dispersion, the 1 g (gram) of oil is divided into 1 micron droplets, which leads to properties such as F(q)>>F(g) (electrostatic forces are orders of magnitude greater than the gravitational forces), and the M/q(charge), M/ST(surface tension) and SA(surface area)/V(volume) ratios are all inverted from those observed in the single large droplet. In this second case of a dispersed oil sample, the droplets of oil will behave more or less as elastic to pseudoplastic particles. Unlike any other filtration substrates or media, the MAC infused filtration media is able to overcome the ST of small droplets in this regime converting them to liquid phase behavior. Viscoelasticity of the cohesive mass (the combined MAC and oil) allows for practically zero ΔP through the filter upon capturing of the oily mist. Further, the cohesiveness of the capturing materials prevents re-entrainment and/or any splattering effects up to complete saturation of the filter, which is approximately 20 to 30 times the w/w % (wt %) oil, which also reduces or eliminates any odor transmission. Therefore, these two states are diametrical opposites in properties and behavior yet the filtration media of the present disclosure is capable of capturing and immobilizing either state, and a continuous range of particle sizes between these two states, without the re-entrainment of the contaminant in the fluid stream. Table 2 continues the comparison of how droplet size affects properties, by illustrating how the ratio of internal to external pressure for water drops of different radii vary (at standard temperature and pressure, STP) from 1 nm to 1000 nm size.

TABLE 1

Two exemplary states of 1 ppm concentration oil contaminant in an aqueous stream (1 g oil in 1 $m^3$ of water) as a function of oil drop size.

| State of 1 ppm oil | 1 drop | 1 micron |
|---|---|---|
| Droplet size | 1.26 cm | 1 micron |
| Total surface area | 0.79 $in^2$ | 60 $ft^2$ |
| Number of drops | 1 | 200,000,000,000 ($2 \times 10^{11}$) |
| Charge (q)-to-mass (m) ratio | q<<m Will not exhibit significant electrostatic properties | q>>m Droplets will electrostatically repel each other and resist coalescence |
| Surface tension (ST)-to-mass (m) ratio | ST<<m | ST>>m |
| g/m (apparent density versus water) | Will float and will disperse with minimal agitation | Neutrally buoyant individual droplets will behave like solid particles; ST can only be overcome chemically or with heat |
| General behavior | Will behave like a liquid | Will behave like a particle |
| Appearance | Clearly visible sheen, clear under O/W interface | No distinct O/W interface, cloudy, dark or milky appearance opaque |

TABLE 2

Ratio of internal to external pressure for water drops of different radii at standard temperature and pressure (STP)

| Droplet radius (nm) | 1000 | 100 | 10 | 1 |
|---|---|---|---|---|
| Internal/external pressure ratio | 1 | 1 | 1.1 | 2.9 |

This distinction between large and small oil droplets illustrates some of the unique and non-obvious features of the present disclosure. While most industrial operators typically are concerned only with concentration of a contaminant in a discharge stream, for example, whether the contaminant is being discharged at 1 ppm, 50 ppm, or 100 ppm concentration, current methods of detecting concentration may completely miss the discharge of a large single droplet of oil in a volume of water as exemplified above, or alternatively, provide a false indication that the actual discharge concentration over time is much greater than it is.

The visual quality indicator (VQI) device and technology disclosed herein are unique in being capable of detecting 1 ppm, for example, in both regimes, and at the same time. The VQI can be used in aid of characterization and to demonstrate in the first place that there is oil present. Standard sampling for chemical or instrumental analysis often fails to detect oil when it is not well dispersed. When oil is detected it is a high positive error and this is perceived as an acute event as opposed to a steady state situation. The VQI, which is effectively a time weighted trap, allows for easy visual detection of effective concentrations well under 1 ppm. The ratio of dispersed to non-dispersed oil can be approximated visually by observation of a cross-sectional filter coupon or by other chemical or physical techniques and can be used to justify the relative weighting of process stream components. The trap aspect also allows for easy trouble shooting in many cases, such as when banks of heat exchangers are employed and one is leaking causing pollution of the entire system. Normally, it could take days to find the leaky culprit, but by having a VQI side streamed at the effluent of each unit, a leaky exchanger can be readily identified, isolated if desired to prevent shutdown of the entire array, and repaired before a more serious problem develops.

Thus, the state of the oily contaminant is an important consideration in designing the optimal process stream, and obtain such information requires the user to have the best tools and methods for accurate characterization and treatment. When the appropriate process stream is employed which matches the state and behavior of the influent, any concentration can be achieved by simply increasing modular capacity.

Because oil droplets impinging upon the surface of the filter of the invention are immobilized into a viscoelastic mass, they do not then spread uniformly throughout such surface. This feature provides a useful operational feature, because large drops are readily distinguishable from swarms of minute, highly dispersed droplets, by simple operator observation through the transparent window. The latter collection of many highly dispersed droplets can be observed as a uniform discoloration of the filter surface, while the former large drop contaminant presents as one or more visible enlarged spots. One significance of this feature is that other types of evaluations based on, for example, measurement of oil concentration (ppm) in a grab sample of the flow of interest can be vastly inaccurate where mainly large oil drops are contained in the sample. Thus while the actual ppm of oil contaminating two separate flows may be identical, measurements of samples from each flow can provide vastly different results depending on the drop size and degree of dispersal of the oil drops in the two cases. In the present invention, however, mere direct observation of the capturing filter surface of the VQI will provide guidance to the operator as to the real character of the contamination.

In some embodiments, the visual indicator apparatus is applicable to filtration of bilge water, but other embodiments are also applicable where the media to be examined is any aqueous stream, such as an aqueous process stream, water coolant stream, or the like. In many applications, the filtration system can include at least a second (or "secondary") filtration stage in series with the first stage; each filtration stage being provided with the said filtration media. The bypass line is connected between the output line from the first stage and the flow output line from the downstream second stage; the said visual quality indicator (VQI) comprising a pair of the filtration status chambers serially connected in the bypass line. Visible oil at the first status chamber indicates saturation of the first filtration stage, allowing optimization of filter use efficiency. The second status chamber is always kept transparent until complete loading and supersaturating breakthrough of the first status chamber due to the ability of the filtration media to permanently capture oil without re-entrainment. Therefore, the absence of oily contaminants in the downstream of the two status chambers indicates that there has not been a breakthrough of oily contaminants from the first to the second filtration stage and thus that the output flow from the filtration system is substantially free of the oily contaminants. Alternatively, the presence of visually discernible oily contaminants at both of the filtration chambers indicates that there has been a breakthrough of the oily contaminants from the first filtration stage, which therefore is in need of servicing. Moreover, in the present invention, any supersaturating breakthrough that is detected at the visual quality indicator is breakthrough of the viscoelastic coagulated mass formed from the oil and the MAC, that is, this viscoelastic contaminant is immobilized at the filtration media of the status chamber, and no uncoagulated contaminant can break through.

In a further aspect, this disclosure is more generally applicable to detection of oily contaminants in any industrial process stream, where the presence of such oily elements is indeed undesired, as for example where the contaminants are indicative of a leakage. This is illustrated by the use of the invention in a heat exchanger system involving, for example, a hot process stream and a coolant stream. Oily components intended to be present in only one of the streams can, as a result of system wear and failure, leak into the other stream. The invention renders it possible to quickly detect the presence of the contaminant in the stream where it should not be present. This can be particularly valuable where the heat exchanger system employs numerous individual heat exchangers together with a recirculating coolant stream. Commonly with such a system, the individual coolant streams from a bank of individual exchangers are merged for subsequent recirculation to the individual exchangers. The presence of oily contaminants in the merged stream does not of itself indicate which of the individual exchangers is (or are) the source of the leakage. However, by emplacing the VQI devices of the invention in each of the coolant streams at the individual exchangers, it becomes possible to readily ascertain the leakage source or sources by a simple and direct visual inspection of the said devices.

BRIEF DESCRIPTION OF DRAWINGS

The invention is diagrammatically illustrated, by way of example, in the drawings appended hereto, in which.

DESCRIPTION OF PREFERRED EMBODIMENTS

Figure 1:
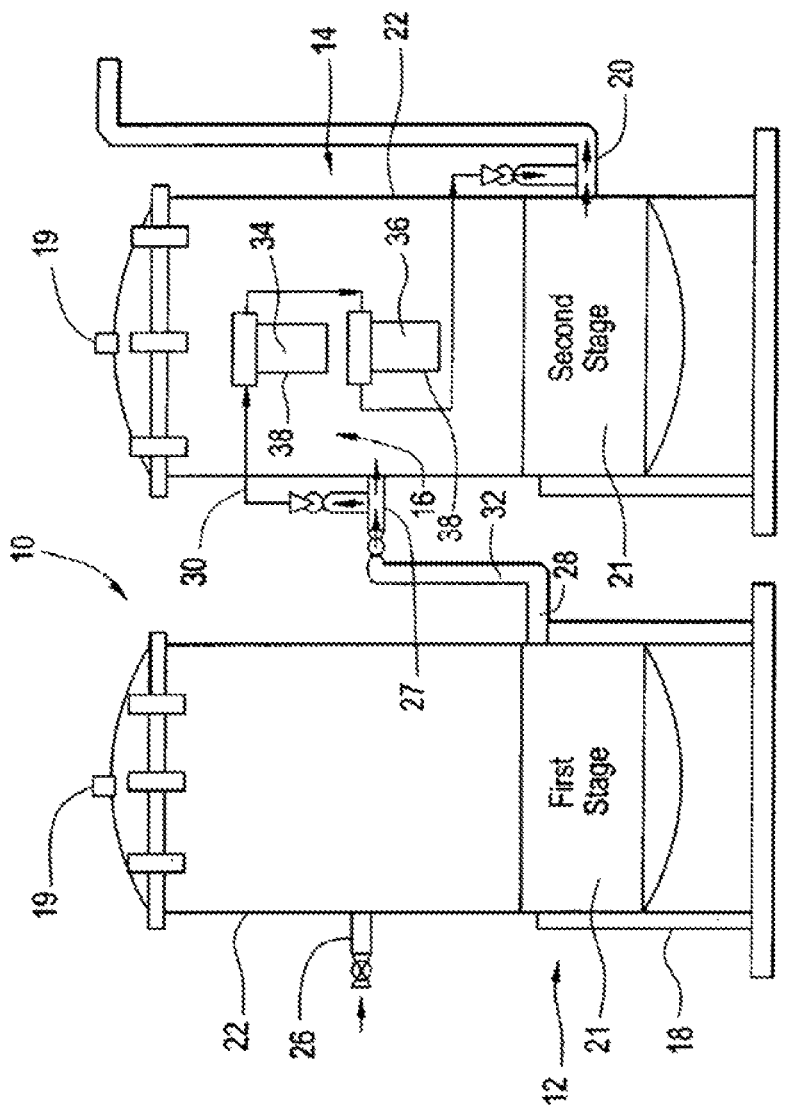
FIG. 1 is a simplified schematic elevational view of a water filtration system incorporating a visual water quality indicator in accordance with the present invention.

In preferred embodiments of the disclosure, a visual quality indicator device ("VQI") is provided for determining the presence of oily contaminants in an aqueous stream. The VQI includes a status chamber having an inlet and an outlet for receiving and discharging the aqueous stream, and a transparent wall enabling viewing of the chamber interior. A fluid-pervious filtration media is present within the chamber, which has been infused with an absorption composition comprising a homogeneous thermal reaction product of an oil component selected from the group consisting of glycerides, fatty acids, alkenes, and alkynes, and a methacrylate or acrylate polymer component; the contaminant on contact with the media being thereby immobilized. The media has a surface viewable through the transparent wall, and the stream flow path is such as to cause the stream to impinge at the media via the surface, whereby the contaminants collect selectively at said surface and are therefore highly visible through the transparent wall.

The filtration status chamber can have means for channeling the flow received therein from the chamber lateral walls toward its central axis, whereby the oily contaminants in the flow collect selectively at the outer portions of the filtration media, which are highly visible to an operator or observer of the system. The media preferably includes a highly visible fluorescent or phosphorescent dye or pigment, whereby the presence of captured oily contaminants is visually enhanced. Moreover, the transparent walls of the status chamber may be substantially transparent to UV radiation, whereby the external visibility of contaminants collected at said filtration media may be augmented by rendering UV light incident on the media from an external UV source.

The fluid-pervious filtration media may comprise any of the MAC infused materials cited for that purpose in the present applicant's aforementioned U.S. patents, including where such materials are formed into a sheet or web.

In a further aspect, the invention comprises a method for visually determining the presence of oily contaminants in an aqueous stream.

In a first embodiment of the invention illustrated in the drawings, a visual quality indicator (VQI) is provided and described for its use with any source or stream of water such as bilgewater or an aqueous industrial process stream. The arrangement depicted utilizes a by-pass shunt composed of two VQI filtration status chambers in series, each of which are provided with fluorescent or phosphorescent dye- or pigment-treated filtration media. These filters can be of the types discussed in U.S. Pat. No. 6,475,393 patent, except that in the present arrangement the filtration media is also treated with a fluorescent or phosphorescent dye having very high visibility such as a "hot pink". The filters can also be of the types disclosed in the present inventor's U.S. Pat. Nos. 7,264,721 and 7,264,722, if desired.

Therefore, the claimed combination of (1) a transparent outer wall of the filtration status chamber; (2) a radially inward flow of the aqueous stream being monitored; and (3) a very specific filtration media that is the homogeneous thermal reaction product of an oil component and a methacrylate or acrylate polymer component, allows droplets of viscoelastic contaminant to be readily immobilized and immediately visualized at very low concentrations. Oil droplets as small as one micron, are captured and immobilized by the primary filter and are instantly visible against the hot pink or similar high visibility background of the exemplary dye previously mentioned. Due to the ability of the infused media to permanently capture oil without re-entrainment, the secondary filter chamber is always kept transparent until complete loading, and supersaturating breakthrough of the viscoelastic cohesive mass of the primary chamber. Oil droplets as small as one micron, are captured and immobilized by the primary filter and are instantly visible against the hot pink or similar high visibility background of the exemplary dye previously mentioned. Due to the ability of the infused media to permanently capture oil without re-entrainment, the secondary filter chamber is always kept transparent until complete loading, and supersaturating breakthrough of the primary chamber. Oily droplet visibility can be further enhanced with ultraviolet illumination as mentioned.

This novel combination of features provides that the filtration media infused with the claimed composition intercepts an oil droplet and denatures it into a viscoelastic, viscous mass immobilized on the visible external surface. The oil droplet will not further disperse, but remains immobilized thereby providing valuable diagnostic information about the system. Other prior art devices such as coalescer devices merely coalesce oily contaminants, but typically the coalesced oil will disperse or disperse and re-coalesce on the filter until released in both small and large droplets, giving the same amount of discoloration for both droplet states, if any discoloration is indicated at all. In contrast, the claimed visual quality indicator can distinguish the 1 micron droplets, which will uniformly darken the surface of the indicator, and a single 1 mL drop which will immobilize and remain visible without dispersing and spreading through the filter.

Thus, the present disclosure provides for a visual quality indicator (VQI) device for determining the presence of oily contaminants in an aqueous stream, the VQI device comprising:

a status chamber having an inlet and an outlet for receiving and discharging said aqueous stream, and a transparent wall enabling viewing of the chamber interior;

a fluid-pervious filtration media within said chamber, which has been infused with an absorption composition comprising a homogeneous thermal reaction product of an oil component selected from the group consisting of glycerides, fatty acids, alkenes, and alkynes, and a methacrylate or acrylate polymer component, the contaminants on contact with said media being thereby immobilized; and said media having a surface viewable through said transparent wall, the said chamber providing a stream flow path to cause the aqueous stream to impinge at the media via the surface of the media, whereby said contaminants collect selectively at said surface and are highly visible through said transparent wall.

Therefore, in one aspect, the VQI device includes a status chamber and a means for channeling the stream flow received therein from the status chamber lateral walls toward its central axis, whereby said oily contaminants in the flow collect selectively at the outer portions of the filtration media which are highly visible to an observer or operator. According to some embodiments, the filtration media of the VQI can include a highly visible fluorescent or phosphorescent dye or pigment, whereby the presence of immobilized oily contaminants is visually enhanced. In this latter aspect, the transparent wall of the VQI device can be substantially transparent to UV radiation, whereby the external visibility of contaminants collected at said filtration media may be augmented by rendering UV light incident on said filtration media from an external UV source.

Figure 2:
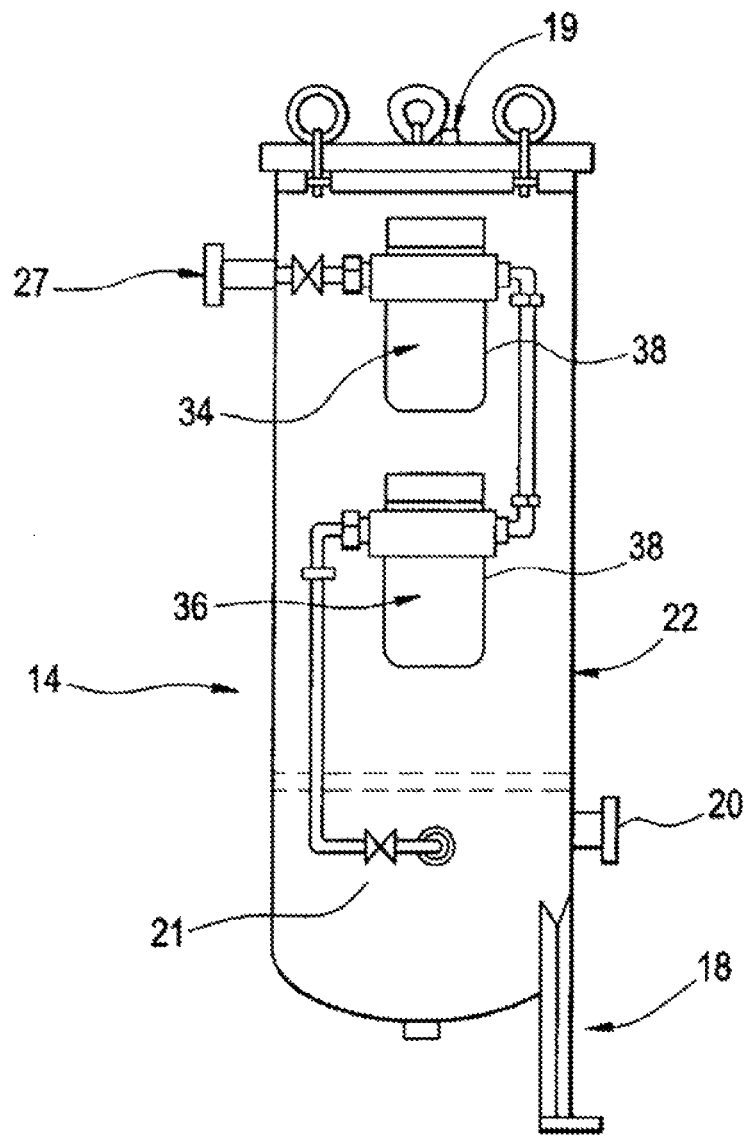
FIG. 2 is a simplified schematic elevational view of the second filtration stage portion of the system of FIG. 1.

To illustrate the operation of the VQI of this disclosure, the schematic view of FIG. 1 shows a water treatment unit 10 with which the present invention may be utilized. The FIG. 1 embodiment is applicable to, for example, a bilgewater treatment unit and method. Unit 10 is composed of two in series filtration stages 12 and 14, and is deployed following one or more conventional OWS units (Oily Water Separators; not shown) in order to ensure discharge of no greater than around 15 ppm oil. Legs 18 are affixed to each support stages 12 and 14. The primary stage 12 receives the flow from the OWS at its input port 26 and removes the bulk of the oil loading. The secondary stage 14 receives the output flow from stage 12 and polishes any breakthrough as necessary. These units are self-activating, and are not consumed outside the presence of oil. The visual indicator generally shown at 16 is driven by the pressure difference between the effluent port 28 of the first stage 12 and the effluent port 20 of the second stage 14. The visual indicator 16 allows one to visually inspect the quality of the effluent leaving the first filtration stage 12 and the degree of loading being imparted to the second filtration stage 14 filters and the degree of saturation of the primary filtration stage 12. A 15-ppm conventional oil content monitor (OCM) is provided (not shown) at the final discharge point from unit 10 and controls the OWS unit or units. This visual inspection allows one to correlate the OCM reading with the visual appearance of the first chamber effluent. Use of the visual indicator 16, allows one to monitor effluent quality, filter loading and degree of emulsification. Also illustrated at FIG. 2 is a simplified schematic elevational view of the second filtration stage portion of the system of FIG. 1.

Figure 3:
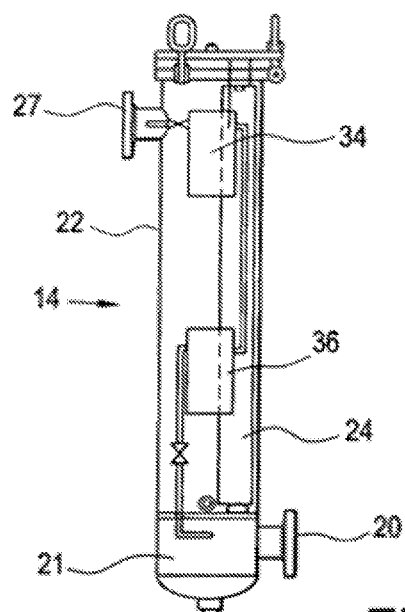
FIG. 3 is a further schematic elevational view of the second filtration stage portion of the system of FIG. 1, but showing additional features of the filtration stage and the visual quality indicator associated therewith.
Figure 3A:
FIG. 3A is a top plan view of the device of FIG. 3.
Figure 3B:
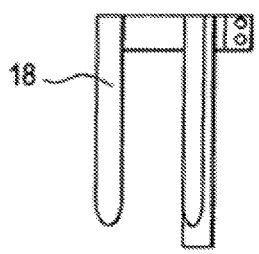
FIGS. 3B and 3C are plan and elevational views of the support means used with the FIG. 3 device.
Figure 3C:
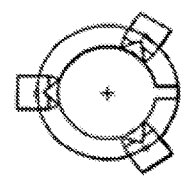

The filtration stages 12 and 14 with which the invention is used are per se devices which are generally of types which are commercially available from the Mycelx Corporation, assignee of the present invention, except that the connections to these stages have been modified to enable incorporation of the visual inspection device 16 of the present invention. Referring for example to FIG. 3, the filtration stage 14 is shown as including an outer shell 22 which internally houses in this illustration four filter cartridges, one of which is seen at 24. Stage 12 similarly includes four such filter cartridges. The filtration cartridges 24 are of the type disclosed in the present inventor's U.S. patents as discussed in the foregoing disclosure. Each filtration stage 12 and 14 is provided with a top vent 19 and a bottom fluid collection volume 21. The stream to be treated, for example from the OWS, enters at the input port 26 of stage 12 and after flowing through the in parallel filter cartridges 24 and collecting in volume 21, exits at output port 28 and then passes through line 32 to input port 27 of stage 14. It is seen however that a bypass line or shunt 30 is provided where the connection line 32 enters the second filtration stage 14 so that a test stream may be diverted outside shell 22 of the second stage and thence through two in series connected filtration status chambers 34 and 36, each of which is provided with a transparent shell 38 formed of a tough plastic material such as a polycarbonate.

Figure 4:
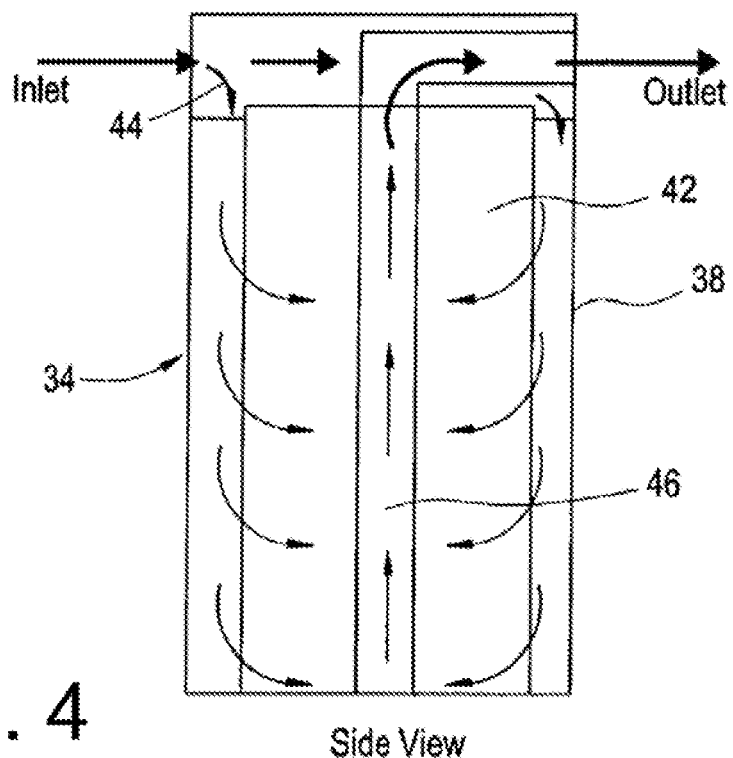
FIG. 4 is a simplified schematic longitudinally cross-sectioned view through one of the filtration status chambers used in the present invention.
Figure 4A:
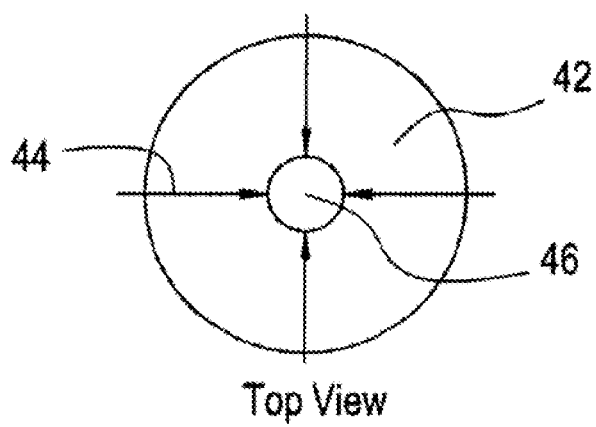
FIG. 4A is a schematic transverse cross section of the FIG. 4 chamber, which has been simplified by not including the outer shell, so as to better show the flow pattern through the chamber.

The VQI filtration status chambers 34 and 36 utilize as filtration media 42 the same absorbent media as in the present inventor's above-cited patents. It is further, however, important for the invention to provide a flow 44 through the chambers which starts at the portions of the filtration media adjacent the chamber outer wall 38 and proceeds radially inward toward the chamber axis 46 where it is collected and then exits. This flow pattern (which for chamber 34 is seen in the simplified schematic views of FIGS. 4 and 4A) assures that discoloration caused by oil in the aqueous stream which is collected at the filtration media will rapidly become evident to the operator who views the chambers externally through the transparent walls of each. Visible oil at the first detection chamber indicates saturation of the first stage bilge treatment cartridge filters, allowing optimization of filter use and efficiency. The arrangement of the invention thereby prevents premature changeover of filters and allows detection of breakthrough.

In a further aspect of the invention, the filtration media 42 in the status chambers 34 and 36 preferably include a highly visible fluorescent or phosphorescent dye or pigment, such as a "hot pink", "fluorescent yellow-green", or bright yellow dye or pigment. This not only assures that the operator can readily see even a slight discoloration produced by captured oil droplets, but permits further augmentation and amplification of visibility effects by the expedient of illuminating the media with UV light by rendering such radiation incident at the media through the visually transparent walls 38, which are also selected to be substantially transparent at the UV wavelengths used.

The VQI filtration status chambers 34 and 36 described in the foregoing in connection with bilgewater filtration, are equally applicable for use of any type of aqueous stream or with gaseous streams. Particularly where the test stream is gaseous, the filtration media 42 can readily be a MAC-infused sheet or web, which in some instances may be supported over a gas-pervious annular cylinder, such a metal or plastic annular cylinder with perforated walls or one formed from a metal or plastic screen.

Figure 5:
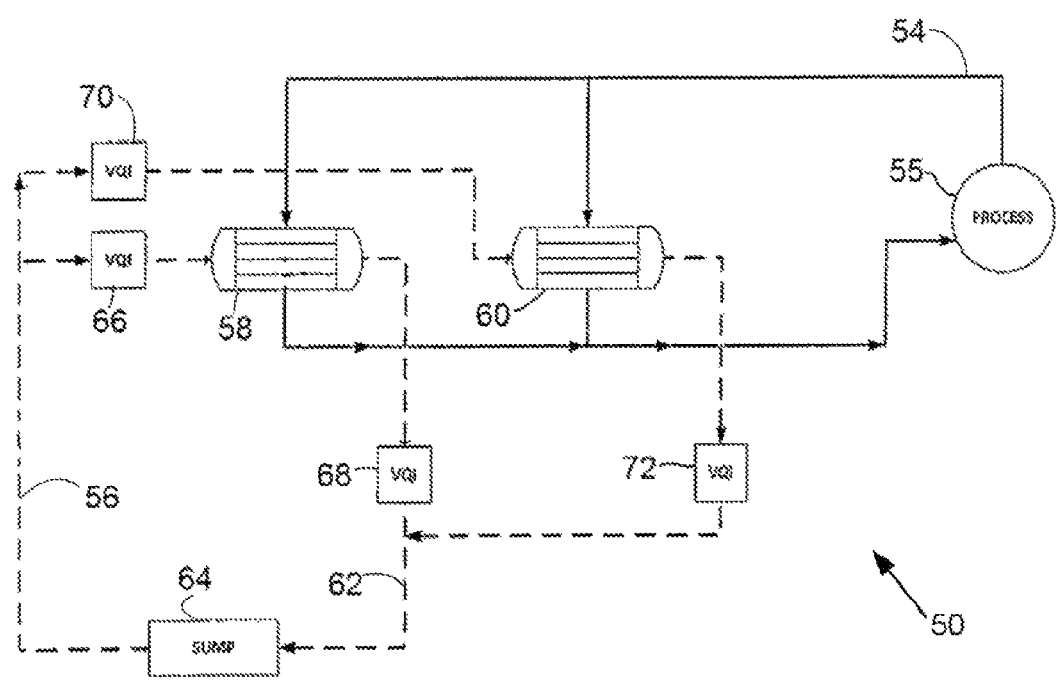
FIG. 5 is a simplified schematic view of a heat exchanger system incorporating visual quality indicators in accordance with the present invention.

The invention is generally applicable to detection of oily contaminants in any industrial process stream or other aqueous stream, where the presence of such oily elements is undesired, as for example where the contaminants are indicative of a leakage, for example, from a stream containing oily contaminants to an aqueous stream which is normally free of such contaminants. This general applicability is illustrated in FIG. 5, which provides a simplified schematic view of a heat exchanger system incorporating visual quality indicators in accordance with the present disclosure. Thus, FIG. 5 illustrates the use of the VQI of this disclosure in a heat exchanger system 50, involving for example a hot process stream 54 and a coolant stream 56. Oily components in FIG. 5 are assumed to be present in only one of the streams, that is, the hot process stream 54 which can be, for example, a process stream in an oil refinery, a chemical plant, or the like, or a produced water stream from an oil well operation. However, as a result of system wear and tear and eventual failure, leakage into the coolant stream can occur in the heat exchangers in which the heat transfer is effected. The VQI of this disclosure enables the operator to quickly detect the presence of the contaminant in the coolant stream and localize the source of the leak. The heat exchanger system 50 in FIG. 5 is typical of an industrial process arrangement in employing a bank of individual heat exchangers connected in series and/or in parallel.

Representatively, two such heat exchangers 58 and 60 are shown connected in parallel. In practice, a much larger number of heat exchangers may be provided than illustrated in FIG. 5. Each exchanger receives the recirculating process stream 54 from process 55 as well as a branched flow of recirculating coolant stream 56. Commonly with such a system, the individual coolant streams proceeding from the bank of individual exchangers are merged (for example, shown here at a common line 62), as coolant water is provided to a sump 64 for subsequent recirculation to the individual exchangers A difficult issue is presented for the operator if only the merged stream in line 62 is tested for the presence of oily contaminants, since the presence of such oily contaminants in the merged stream does not establish which of the individual exchangers is (or are) the source of the leakage. Ideally, upon detecting oily contaminants in the merged stream, the operator would assume a leak at one or more of the exchangers, but simple and rapid means to locate the defective unit or units were not economically available. This difficulty is obviated by the VQI described in the present disclosure. Thus by emplacing the VQI devices of the invention in each of the coolant streams at the individual exchangers, it becomes possible to ascertain the specific leakage source or sources by a simple and direct visual inspection of the said devices. Preferably, as seen in FIG. 5, separate pairs 66, 68 and 70, 72 of VQIs are disposed at the input and output sides of each heat exchanger 58 and 60 to facilitate certainty as to the condition of the exchanger involved.

The VQIs in FIG. 5 can have any of the configurations disclosed in the present specification, and the process stream and/or the coolant stream can be either aqueous or gaseous. It will also be appreciated that in the system of FIG. 5 the oily components originate in the hot stream, it being assumed that the issue involved is that of possible leakage to the coolant stream. However, in other instances such components could originate in the cooler stream, so that leakage would be an issue where the hotter stream was found to be acquiring such oily components; and in such event the VQIs would be employed in a similar manner at the hotter stream or streams.

Therefore, there is also provided in this disclosure for a method for determining the presence of oily contaminants in an aqueous stream, the method comprising:

flowing said aqueous stream through a filtration status chamber having an inlet and an outlet for receiving and discharging said aqueous stream, and a transparent wall enabling viewing of the chamber interior;

said chamber being provided with a fluid-pervious filtration media which has been infused with an absorption composition comprising a homogeneous thermal reaction product of an oil component selected from the group consisting of glycerides, fatty acids, alkenes, and alkynes, and a methacrylate or acrylate polymer component, the contaminants on contact with said media being thereby immobilized;

said media having a surface viewable through said transparent wall, the said chamber providing a stream flow path to cause the aqueous stream to impinge at the media via the surface, whereby said contaminants collect selectively at said surface and are highly visible through said transparent wall.

In embodiments of this method, the filtration status chamber can have means for channeling the stream flow received therein from the chamber lateral walls toward its central axis, whereby said oily contaminants in the flow collect selectively at the outer portions of the filtration media which are highly visible to an operator. In further embodiments, the said aqueous stream is a by-passed test stream taken from a primary stream for which the presence of said oily contaminants is being evaluated. If desired, the said aqueous stream can be a test stream formed from the content of a receptacle of an aqueous liquid.

As illustrated herein, this disclosure also provides a system for exchanging heat content in a process between an aqueous process stream containing oily contaminants and a normally oil-free fluid stream, such as an aqueous, gaseous, or other fluid stream, said system including:

(a) a plurality of heat exchangers;
(b) means for dividing the aqueous process stream into a plurality of first substreams and means for dividing the normally oil-free aqueous stream into a plurality of second substreams;
(c) means for passing one of each of said first and second substreams through one each of the plurality of heat exchangers where heat transfer can occur;
(d) means for reuniting the plurality of first substreams and returning the reunited aqueous process stream to the process, and means for reuniting the plurality of second substreams and returning the reunited normally oil-free aqueous stream for recirculation to said heat exchangers; and
(e) a visual quality indicator (VQI) device adapted for determining the presence of oily contaminants in an aqueous stream, being positioned downstream of each of said heat exchangers to receive at least a portion of the respective second substream having passed through the heat exchanger, whereby direct visual inspection of each of said VQI devices can enable identification of any of the heat exchangers at which oil leakage may have occurred between the first and the second substreams;
(f) said VQI device comprising:
(i) a filtration status chamber having an inlet and an outlet for receiving and discharging said aqueous stream, and a transparent wall enabling viewing of the chamber interior;
(ii) a fluid-pervious filtration media within said chamber, which has been infused with an absorption composition comprising a homogeneous thermal reaction product of an oil component selected from the group consisting of glycerides, fatty acids, alkenes, and alkynes, and a methacrylate or acrylate polymer component, the contaminants on contact with said media being thereby immobilized; and
(iii) said media having a surface viewable through said transparent wall, the said chamber providing a stream flow path to cause the aqueous stream to impinge at said surface of the said media, whereby said contaminants collect selectively at said surface and are highly visible through said transparent wall.

In various embodiments, the means for dividing the aqueous process stream into a plurality of first substreams can be located downstream of the process, and the means for dividing the normally oil-free aqueous (or other fluid) stream into a plurality of second substreams can be located downstream of a fluid supply.

In accordance with this aspect, the various means for dividing the aqueous process stream into a plurality of first substreams and the means for dividing the normally oil-free aqueous stream into a plurality of second substreams can be any structure or structures as understood by the person of ordinary skill to accomplish the stated process of dividing. Such means for dividing may be quite simple and can include, for example, any device that regulates, directs, or controls the flow of the fluid of that particular stream (gases, liquids, fluidized solids, or slurries) by opening, closing, splitting, or partially obstructing various passageways, which can include valves, valves fittings, flow splitters, weirs, joints, branches, and the like. Complex valves, fittings, and combinations of these means can be used, such that they can be operated manually or automatically, or constitute permanent fixtures to regulate, direct, or control the fluid flow.

Also in accordance with this aspect, the various means for passing one of each of said first and second substreams through one each of the plurality of heat exchangers can be any of the means as understood by the person of ordinary skill to accomplish the process of passing the fluid through the heat exchangers where heat transfer can occur. Such means for passing can include, for example, any of the structures used in heat exchangers for heat transfer from one fluid to another, such that the fluids remain separated by a fluid impermeable wall so they do not mix or come into direct contact. Such means include but are not limited to, those structures and devices widely used in heat exchanging systems in space heating, refrigeration, air conditioning, power plants, chemical plants, petrochemical plants, petroleum refineries, natural gas processing, sewage treatment, and the like. Thus, the means for passing can be structures as may be found in counter-current flow heat exchangers, concurrent flow heat exchangers, spiral flow and/or cross flow heat exchangers, distributed vapor and spiral flow heat exchanges such as found in condensers, and the like. Examples of these types of means for passing can be found in, shell and tube heat exchangers, plate heat exchangers, plate and shell heat exchangers, plate and fin heat exchangers, pillow plate exchangers, and the like.

Further in accordance with this aspect, the means for reuniting the plurality of first substreams and returning the reunited aqueous process stream to a point upstream of the process, and means for reuniting the plurality of second substreams and returning the reunited normally oil-free aqueous stream for recirculation to said heat exchangers can be similar to the various means for dividing the aqueous process stream and the normally oil-free aqueous stream disclosed herein. These means can be any structure or structures as understood by the person of ordinary skill to accomplish the stated process of reuniting substreams and returning their flow as stated. Such means can include, for example, structures or devices that regulate, direct, or control the flow of the fluid of that particular stream (gases, liquids, fluidized solids, or slurries) by opening, closing, splitting, or partially obstructing various passageways, which can include valves, valves fittings, flow splitters, joints, branches, and the like. Complex valves and fittings may be included in these means, such that they can be operated manually or automatically, or constitute permanent fixtures to regulate, direct, or control the fluid flow.

Thus, as further illustrated herein, this disclosure provides, in a system for exchanging heat content in a process between an aqueous process stream containing oily contaminants and a normally oil-free fluid stream, such as a normally oil-free aqueous stream, by dividing the process stream, for example downstream of the process, into a plurality of first substreams and dividing the normally oil-free fluid stream, for example downstream of a fluid supply, into a plurality of second substreams;

passing one of each of said first and second substreams through one each of a plurality of heat exchangers where heat transfer can occur;

reuniting the plurality of first substreams, for example downstream of said heat exchangers, and returning the reunited aqueous process stream to the process, for example to a point upstream of the process, and reuniting the plurality of second substreams, for example downstream of said heat exchangers, and returning the reunited normally oil-free fluid stream for recirculation to said heat exchangers, for example to a point upstream of the heat exchangers:

Other aspects of this disclosure also provide a method enabling rapid visual identification of any of the plurality of said heat exchangers where oil leakage may have occurred between the first and the second substreams at the associated heat exchanger, the method comprising:

(a) positioning a visual quality indicator (VQI) device adapted for determining the presence of oily contaminants in an aqueous stream, downstream of each of said heat exchangers to receive at least a portion of the respective second substream having passed through the heat exchanger, whereby direct visual inspection of each of said VQIs can enable identification of any of the heat exchangers in which said oil leakage may have occurred; and (b) said VQI device comprising:

(i) a filtration status chamber having an inlet and an outlet for receiving and discharging said aqueous stream, and a transparent wall enabling viewing of the chamber interior;

(ii) a fluid-pervious filtration media within said chamber, which has been infused with an absorption composition comprising a homogeneous thermal reaction product of an oil component selected from the group consisting of glycerides, fatty acids, alkenes, and alkynes, and a methacrylate or acrylate polymer component, the contaminants on contact with said media being thereby immobilized; and (iii) said media having a surface viewable through said transparent wall, the said chamber providing a stream flow path to cause the aqueous stream to impinge at said media via said surface, whereby said contaminants collect selectively at said surface and are highly visible through said transparent wall.

As in other embodiments, in these aspects and embodiments, the said filtration status chamber can have means for channeling the stream flow received therein from the chamber lateral walls toward its central axis, whereby said oily contaminants in the flow collect selectively at the outer portions of the filtration media which are highly visible to an observer or operator. That is, contact with the filtration media occurs via the surface of the media, thereby allowing visualization of the contaminants. The fluid-pervious filtration media can be in the form of a sheet or a web. Also in this method, the method can further include positioning a VQI device in each of said second substream upstream of the heat exchanger to which it is flowing, thereby providing an additional visual point for comparison with the VQI device positioned in the associated substream downstream of the associated heat exchanger. Thus, typically in this embodiment, the aqueous normally oil-free stream can be a coolant stream for the process stream.

While the present invention has been set forth in terms of specific embodiments thereof, the instant disclosure is such that numerous variations upon the invention are now enabled to those skilled in the art, which variations yet reside within the scope of the present teaching. Thus as already mentioned, while the illustrated embodiment of the invention incorporates two filtration stages, the invention can also be effectively utilized in a single filtration stage system, or in systems employing more than two stages. Similarly it should be clear that the visual indicator of the invention can comprise a single filtration status chamber such a chamber 34 or 36, which can be used in any filtration system, such as a bilge filtration system, where one seeks to effect a visual determination of oily components in the stream flowing through the filtration system. Furthermore, it will be evident that the visual indicator device of the invention can be used to examine aqueous streams other than bilge discharges which carry oily contaminants regardless of the source, as for example streams of this type which are discharged or otherwise handled by industrial facilities or the like.

Accordingly, the invention is to be broadly construed and limited only by the scope and spirit of the present disclosure and the claims appended hereto.

I claim:

1. A system for exchanging heat content in a process between an aqueous process stream containing oily contaminants and a normally oil-free aqueous stream, said system comprising:
   (a) a plurality of heat exchangers;
   (b) means for dividing the aqueous process stream into a plurality of first sub streams and means for dividing the normally oil-free aqueous stream into a plurality of second substreams;
   (c) means for passing one of each of said first and second substreams through one each of the plurality of heat exchangers where heat transfer can occur;
   (d) means for reuniting the plurality of first sub streams downstream of said heat exchangers and returning the reunited aqueous process stream to the process, and means for reuniting the plurality of second sub streams downstream of said heat exchangers and returning the reunited normally oil-free aqueous stream for recirculation to said heat exchangers; and
   (e) a visual quality indicator (VQI) device adapted for determining the presence of oily contaminants in an aqueous stream, being positioned downstream of each of said heat exchangers to receive at least a portion of the respective second substream having passed through the heat exchanger, whereby direct visual inspection of each of said devices can enable identification of any of the heat exchangers at which oil leakage may have occurred between the first and the second substreams;
   (f) said device comprising:
      (i) a filtration status chamber having an inlet and an outlet for receiving and discharging said aqueous stream, and a transparent wall enabling viewing of the chamber interior;
      (ii) a fluid-pervious filtration media within said chamber, which has been infused with an absorption composition comprising a homogeneous thermal reaction product of an oil component selected from the group consisting of glycerides, fatty acids, alkenes, and alkynes, and a methacrylate or acrylate polymer component, the contaminants on contact with said media being thereby immobilized; and
      (iii) said media having a surface viewable through said transparent wall, the said chamber providing a stream flow path to cause the aqueous stream to impinge at said media via said surface, whereby said contaminants collect selectively at said surface and are highly visible through said transparent wall.

2. A system in accordance with claim 1, wherein said filtration status chamber has means for channeling the stream flow received therein from the chamber lateral walls toward its central axis, whereby said oily contaminants in the flow collect selectively at the said surface of the filtration media and are highly visible to an operator.

3. A system in accordance with claim 1, wherein the said filtration media includes a highly visible fluorescent or phosphorescent dye or pigment, whereby the presence of immobilized oily contaminants is visually enhanced.

4. A system in accordance with claim 3, wherein the said transparent wall is substantially transparent to UV radiation, whereby the external visibility of contaminants collected at said filtration media may be augmented by rendering UV light incident on said filtration media from an external UV source.

5. A system in accordance with claim 1, wherein the said fluid-pervious filtration media is the form of a sheet.

6. A system in accordance with claim 1, further including positioning a device in each of said second substreams upstream of the heat exchanger to which it is flowing, thereby providing an additional visual point for comparison with the device positioned in the associated substream downstream of the associated heat exchanger.

7. A system in accordance with claim 1, wherein the normally oil-free aqueous stream is a coolant stream for the process stream.

\* \* \* \* \*